(12) United States Patent
Callan et al.

(10) Patent No.: US 6,610,206 B1
(45) Date of Patent: Aug. 26, 2003

(54) BUFFERED COMPOSITIONS FOR DIALYSIS

(75) Inventors: Robin Callan, Bellevue, WA (US); Walter A. van Schalkwijk, Issaquah, WA (US); James J. Cole, Arlington, WA (US)

(73) Assignee: Advanced Renal Technologies, Bellevue, WA (US)

( * ) Notice: Subject to any disclaimer, the term of this patent is extended or adjusted under 35 U.S.C. 154(b) by 0 days.

(21) Appl. No.: 09/421,622

(22) Filed: Oct. 19, 1999

Related U.S. Application Data

(60) Provisional application No. 60/105,049, filed on Oct. 20, 1998.

(51) Int. Cl.$^7$ .......................... A61K 33/14; A61K 31/19
(52) U.S. Cl. .................. 210/646; 210/647; 514/574; 514/557; 424/665
(58) Field of Search .......................................... 514/557

(56) References Cited

U.S. PATENT DOCUMENTS

| | | | |
|---|---|---|---|
| 3,962,075 A | 6/1976 | Fialkoff et al. | 210/22 A |
| 4,339,433 A | 7/1982 | Kartinos et al. | 424/78 |
| 4,451,454 A | 5/1984 | Wong | 424/127 |
| 4,500,309 A | 2/1985 | Diederich et al. | 604/5 |
| 4,581,141 A | 4/1986 | Ash | 210/502 |
| 4,661,246 A | 4/1987 | Ash | 210/87 |
| 4,663,166 A | 5/1987 | Veech | 424/146 |
| 4,756,838 A | 7/1988 | Veltman | 252/1 |
| 4,784,495 A | 11/1988 | Jonsson et al. | 366/151 |
| 4,879,280 A | 11/1989 | Seyffart et al. | 514/53 |
| 4,886,789 A | 12/1989 | Milner | 514/60 |
| 4,906,616 A | 3/1990 | Gilchrist et al. | 514/21 |
| 4,938,873 A | 7/1990 | Rossi | 210/646 |
| 5,108,767 A | 4/1992 | Mulchandani et al. | 426/72 |
| 5,252,213 A * | 10/1993 | Ahmad et al. | 210/542 |
| 5,474,992 A | 12/1995 | Ogata et al. | 514/100 |
| 5,589,197 A | 12/1996 | Shockley et al. | 424/663 |
| 5,591,344 A | 1/1997 | Kenley et al. | 210/636 |
| 5,624,668 A | 4/1997 | Lawrence et al. | 424/78.17 |
| 5,645,734 A | 7/1997 | Kenley et al. | 210/805 |
| 5,651,893 A | 7/1997 | Kenley et al. | 210/636 |
| 5,658,456 A | 8/1997 | Kenley et al. | 210/85 |
| 5,674,390 A | 10/1997 | Matthews et al. | 210/261 |
| 5,674,404 A | 10/1997 | Kenley et al. | 210/741 |
| 5,690,821 A | 11/1997 | Kenley et al. | 210/195.1 |
| 5,698,100 A | 12/1997 | Levin et al. | 210/321.6 |
| 5,728,678 A | 3/1998 | Trimbo et al. | 514/12 |
| 5,762,782 A | 6/1998 | Kenley et al. | 210/85 |
| 5,780,438 A | 7/1998 | Gilchrist et al. | 514/21 |
| 5,783,072 A | 7/1998 | Kenley et al. | 210/195.2 |
| 5,827,820 A | 10/1998 | duMoulin et al. | 514/2 |
| 5,851,483 A | 12/1998 | Nicolle et al. | 422/28 |
| 5,906,978 A | 5/1999 | Ash | 514/23 |
| 5,945,129 A | 8/1999 | Knerr et al. | 424/676 |
| 6,019,925 A | 2/2000 | Diamantoglou et al. | 264/203 |
| 6,077,836 A | 6/2000 | Milner | 514/54 |

FOREIGN PATENT DOCUMENTS

| | | |
|---|---|---|
| EP | 457 960 A2 | 11/1991 |
| EP | 821 951 A1 | 2/1998 |
| JP | A-8 092 070 | 4/1996 |
| WO | 9601118 * | 1/1996 |

OTHER PUBLICATIONS

WPI Acc. No. 1996–235 949 Abstract of JP–A–8 092 070, Apr. 9, 1996.

J. Van Der Meulen et al., "Citrate anticoagulation and dialysate with reduced buffer content in chronic hemodialysis", *Clinical Nephrology*, 37(1), 1992, (36–41).

* cited by examiner

*Primary Examiner*—Theodore J. Criares
*Assistant Examiner*—Jennifer Kim
(74) *Attorney, Agent, or Firm*—Seed Intellectual Property Law Group PLLC

(57) ABSTRACT

Acid concentrates, and dialysate compositions prepared therefrom, contain citric acid and an effective amount of a buffering agent selected from acetate and/or lactate. The buffering agent allows a physiologically acceptable amount of citrate to maintain the desired pH of the dialysate.

25 Claims, 1 Drawing Sheet

BUFFERED COMPOSITIONS FOR DIALYSIS

CROSS-REFERENCE TO RELATED APPLICATION

This application claims the benefit of priority from U.S. provisional patent application No. 60/105,049, filed Oct. 20, 1998, the entire disclosure of which is hereby incorporated herein by reference.

TECHNICAL FIELD

The present invention relates to therapeutic compositions, and particularly to dialysate compositions.

BACKGROUND OF THE INVENTION

When functioning correctly, the kidneys help the body maintain a normal internal environment called homeostasis. Kidneys help accomplish this normal balance by ridding the body of excess fluids and metabolic waste products (toxins) as well as maintaining precise levels of glucose and electrolytes. Kidney failure can be caused by multiple factors. However, regardless of why a person's kidneys fail, the failure results in the accumulation of excess fluid and toxic waste in that person's body. This uremic poisoning eventually causes death unless the waste material is removed by some artificial means. Hemodialysis is the most common therapeutic measure for a person whose kidneys no longer perform their blood purifying function. Another common type of dialysis is peritoneal dialysis (PD).

Dialysate is the fluid utilized in dialysis, where dialysate serves to 'clean' the blood of kidney failure patients. During hemodialysis, the patient's blood is circulated on one side of a membrane within a dialyzer (i.e., artificial kidney), while dialysate flows on the other side of the membrane. Since blood and dialysate are separated by a semipermeable membrane, movement of molecules can occur between the blood and dialysate. Although the membrane pores are too small to permit blood cells and proteins to leave the blood, the pores allow waste products to be transferred from the blood to the dialysate.

Peritoneal dialysis utilizes the patient's peritoneal membrane as a dialysis membrane. Upon instilling a volume of peritoneal dialysate into the peritoneal cavity, osmotic pressure causes excess fluid and waste products to leave the blood by crossing the peritoneal membrane and accumulate in the peritoneal cavity containing the dialysis fluid. After a sufficient dwell time, the spent peritoneal dialysate together with the accumulated excess fluid and waste products are drained from the peritoneal cavity.

Today, virtually all dialysate for hemodialysis is made at the site of treatment (in a hemodialysis machine) by mixing (1) treated water, (2) an acid concentrate, and (3) a base concentrate. Because the base concentrate typically contains sodium bicarbonate as the primary basic material, dialysate made by mixing these ingredients is commonly known as bicarbonate dialysate. Bicarbonate dialysate is almost universally made in the hemodialysis machine, through the use of a "three-stream" proportionate pumping mechanism wherein the treated water, liquid 'acid concentrate' and liquid bicarbonate (base) concentrate are combined. One patient typically requires 120 liters or more of dialysate for a single hemodialysis treatment. Chronic kidney failure patients are treated 3 times per week, 52 weeks per year.

The concentrates are supplied to the dialysis clinic in two forms; the 'acid concentrate' is generally supplied as a liquid and the bicarbonate is shipped as a dry powder. The acid concentrate typically contains sodium chloride, calcium chloride, potassium chloride, magnesium chloride, dextrose and sufficient acid (acetic acid) for pH balance. The precise composition of the acid concentrate to be used in a specific dialysis session is determined by a doctor's prescription.

Prior to a patient's treatment session, a jug of liquid acid concentrate is obtained. Generally, this jug of concentrate is drawn from a larger tank or drum of the acid concentrate. A staff member of the dialysis clinic also prepares a jug of sodium bicarbonate concentrate by mixing a quantity of powdered sodium bicarbonate with a specific quantity of treated water. Separate concentrated solutions of 'acid' and bicarbonate are necessary because combining concentrated acid and base solutions would cause the precipitation of calcium and magnesium carbonates. After proper mixing, the final dialysate has the concentrations prescribed by the physician.

As noted, kidney failure patients accumulate excess fluids and normally excreted substances in their blood, most notably, blood urea nitrogen (BUN) and creatinine. In fact, the reduction in the blood levels of these two substances is generally used to gauge the efficiency and overall effectiveness of dialysis. Often the efficiency of dialysis can be compromised by a number of factors, one of which could be the blockage of dialyzer membrane pores by clotted blood.

Additionally, many kidney failure patients suffer from chronic acidosis because their kidneys are not able to remove acid. Traditionally, one of the several goals of hemodialysis treatment is the correction of acidosis by providing higher than normal amounts of bicarbonate in the dialysate to buffer the excess acid in the blood. However, despite infusing "extra" bicarbonate during hemodialysis, normal blood bicarbonate levels are not, sustained in many patients between hemodialysis treatments.

Accordingly, there is a need in the art for improved dialysate formulations that increase the efficiency of the hemodialysis treatment. The present invention is directed to meeting this need and provides additional related advantages as disclosed herein.

SUMMARY OF THE INVENTION

The present invention provides compositions, termed dialysate precursor compositions, which may be diluted with water and mixed with a base to thereby form a dialysate composition. The dialysate precursor composition, as well as the dialysate compositions prepared therefrom, contain citric acid and an effective amount of a buffering agent selected from acetate and/or lactate. The buffering agent allows a physiologically acceptable amount of citrate to maintain the desired pH of the dialysate.

In one embodiment, the invention provides a dialysate precursor composition. This composition contains, at a minimum, water; chloride at a concentration ranging from about 1,000 to about 7,000 mEq/L; citrate at a concentration ranging from about 20 to about 900 mEq/L; at least one buffering anion selected from acetate and/or lactate at a concentration ranging from about 0.01 to about 150 mEq/L; and at least one physiologically-acceptable cation.

In another embodiment, the invention provides a dialysate composition. This dialysate composition contains, at a minimum, treated water; chloride at a concentration ranging from about 20 to about 200 mEq/L; citrate at a concentration ranging from about 0.5 to about 30 mEq/L; at least one buffering anion selected from acetate and/or lactate at a concentration ranging from about 0.01 to about 4.5 mEq/L; base including bicarbonate; and at least one physiologically-acceptable cation.

In another embodiment, the present invention provides a method of forming a dialysate precursor composition. The method includes the step of mixing together treated water, chloride, citrate, at least one buffering anion selected from acetate and/or lactate, and at least one physiologically-acceptable cation to provide a composition having chloride at a concentration ranging from about 1,000 to about 7,000 mEq/L, citrate at a concentration ranging from about 20 to about 900 mEq/L, and at least one buffering anion selected from acetate and lactate at a concentration ranging from about 0.01 to about 150 mEq/L.

In another embodiment, the present invention provides a method of forming a dialysate composition. The method includes the step of mixing the dialysate precursor composition with an aqueous bicarbonate-containing solution. The dialysate precursor composition contains, at a minimum, treated water, chloride, citrate, at least one buffering anion selected from acetate and lactate, and at least one physiologically-acceptable cation to provide a concentrate having chloride at a concentration ranging from about 44 to about 143 mEq/L, citrate at a concentration ranging from about 1.5 to about 30 mEq/L, and at least one buffering anion selected from acetate and lactate at a concentration ranging from about 0.01 to about 3.6 mEq/L.

In other embodiments, the present invention provides compositions prepared according to the afore-described methods.

In another embodiment, the present invention provides an aqueous acid-concentrate composition which contains water, chloride at a concentration of about 1,000 to about 7,000 mEq/L; citrate at a concentration ranging from about 20 to about 900 mEq/L; and sufficient physiologically-acceptable cations to provide for a neutral composition. This acid-concentrate composition has a pH of less than 4, and does not contain any of acetate, bicarbonate or lactate.

The magnesium concentration is preferably less than or equal to 2 mEq/L, and the calcium concentration is preferably less than or equal to 4.5 mEq/L, and the bicarbonate concentration is preferably within the range of 25–40 mEq/L. The calcium and magnesium concentrations should be adjusted to higher values as the amount of citrate in the composition increases, in order to compensate for citrate's binding to serum calcium and/or magnesium.

In another embodiment, the present invention provides sterile compositions specifically suited for peritoneal dialysis. According to one embodiment, the invention provides a peritoneal dialysate composition comprising treated water, citrate at a concentration of about 0.5–30 mEq/L; chloride at a concentration of about 20–200 mEq/L; bicarbonate at a concentration of about 5–100 mEq/L assuming all carbonate-containing species are in the bicarbonate form, glucose at a concentration of about 10–100 g/L; and a sufficient number of physiologically-acceptable cations to neutralize all of the citrate, chloride, bicarbonate, and any other anionic species that may be present in the composition. In another embodiment, the invention provides a composition for peritoneal dialysis as described above, but without any water. This embodiment thus provides a dry composition, to which sterile water may be added in order to form a peritoneal dialysate.

BRIEF DESCRIPTION OF THE DRAWING

The FIGURE is a plot of Dialysate pH (y-axis) vs. Sodium Acetate Concentration (x-axis), and shows the effect on pH of adding sodium acetate to dialysate when the bicarbonate concentrate solution had an initial pH of 8.14.

DETAILED DESCRIPTION OF THE INVENTION

Figure 1:
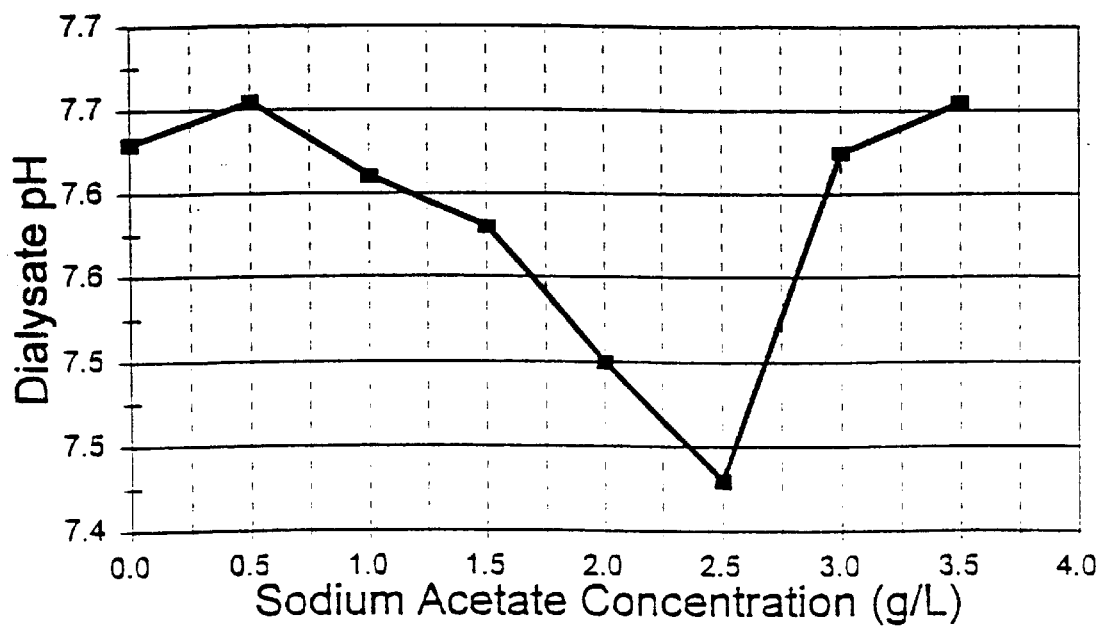

In one aspect, the present invention provides compositions, termed dialysate precursor compositions, which contain, or are prepared from, components including water, chloride, citrate, at least one buffering anion preferably selected from acetate and/or lactate, and at least one physiologically-acceptable cation. The dialysate precursor composition, upon mixing with a base and with dilution, forms a biocompatible composition that can be used for either hemodialysis or peritoneal dialysis.

As discussed in more detail below, the presence of some buffering anion, e.g., an anion selected from acetate and/or lactate, in the dialysate precursor composition allows the dialysate precursor composition to be used as the acid concentrate in a standard three-stream dialysis machine, along with standard base (i.e., bicarbonate) concentrate, thereby mitigating problems associated with fluctuations in the pH of the dialysate during a dialysis treatment. Absent the buffering anion, the dialysate can have pH and/or conductivity properties which are outside the ranges considered acceptable by health care professionals. Prior to a more extended discussion of the compositions of the invention, and the properties thereof, the primary ingredients of the compositions will be described.

As used herein, "chloride" refers to anionic chloride. Thus, the term "chloride" includes anionic chloride and the salt forms thereof, such as may be formed from chloride anion(s) and physiologically-acceptable cation(s). The term "chloride" is not intended to include compounds wherein the chloride atom is covalently bonded to, for example, a carbon atom in an organic molecule. Exemplary physiologically-acceptable cations include, without limitation, hydrogen ions (i.e., protons), metal cations, and ammonium cations. Metal cations are generally preferred, where suitable metal cations include, but are not limited to, the cationic forms of sodium, potassium, magnesium and calcium. Of these, sodium and potassium are preferred, and sodium is more preferred. A composition containing chloride salts may contain a mixture of physiologically-acceptable cations.

In one embodiment, the chloride in the precursor dialysate composition is present at a concentration ranging from about 1,000 to about 7,000 mEq/L, preferably from about 2,000 to about 5,000 mEq/L. In general, the concentrations of the components of present precursor dialysate composition are individually prescribed by a physician to reduce, increase, or normalize the concentrations of various components of the patient's blood, plasma, or serum. Accordingly, the precise concentration of chloride in the precursor dialysate composition, and the dialysate composition prepared therefrom, will be determined by a physician accordingly to principles known in the art.

As used herein, "citrate" refers to a citrate anion, in any form, including citric acid (citrate anion complexed with three protons), salts containing citrate anion, and partial esters of citrate anion. Citrate anion is an organic, tricarboxylate with the following chemical formula:

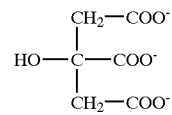

Citric acid, which has been assigned Chemical Abstracts Registry No. 77-92-2, has the molecular formula HOC(CO$_2$H)(CH$_2$CO$_2$H)$_2$ and a formula weight of 192.12 g/mol. A citrate salt (i.e., a salt containing citrate anion) is composed of one or more citrate anions in association with one or more physiologically-acceptable cations. Exemplary physiologically-acceptable cations include, but are not limited to, protons, ammonium cations and metal cations. Suitable metal cations include, but are not limited to, sodium, potassium, calcium, and magnesium, where sodium and potassium are preferred, and sodium is more preferred. A composition containing citrate anion may contain a mixture of physiologically-acceptable cations.

A partial ester of a citrate anion will have one or two, but not all three, of the carboxylate (i.e., —COO⁻) groups of citrate anion in an ester form (i.e., —COO—R, where R is an organic group). In addition to one or two R groups, the partial ester of a citrate anion will include one or two physiologically-acceptable cations (so that the total of the R group(s) and cation(s) equals three). The R group is an organic group, preferably a lower alkyl.

The citrate is preferably in association with protons and/or metal cations. Exemplary of such citrate compounds are, without limitation, citric acid, sodium dihydrogen citrate, disodium hydrogen citrate, trisodium citrate, trisodium citrate dihydrate, potassium dihydrogen citrate, dipotassium hydrogen citrate, calcium citrate, and magnesium citrate. In one embodiment, the citrate is present in the dialysate precursor composition in the form of one or more of citric acid, sodium dihydrogen citrate, disodium hydrogen citrate, potassium dihydrogen citrate, or dipotassium hydrogen citrate.

In a preferred embodiment, citric acid provides the source for the citrate anions. In this embodiment, the citric acid functions as the main acidifying agent of the precursor composition. Citric acid is a relatively inexpensive physiological acid that, under ambient conditions, is in the form of a dry chemical powder, crystal, pellet or tablet. Any physiologically tolerable form of citric acid may be used to introduce citrate anions to the composition. For instance, the citric acid may be in the form of a hydrate, including a monohydrate.

Citrate has been previously recognized to be able to function as an anti-coagulant in the bloodstream by binding calcium. Accordingly, the citrate concentration of the dialysate precursor composition should be selected in view of its anti-coagulation properties. Unless other measures are taken, the citrate concentration should not exceed about 900 mEq/L, and is preferably not more than about 200 mEq/L. When citrate concentrations of 200–900 mEq/L are employed, the magnesium and/or calcium concentration of the dialysate precursor composition must be increased.

Although the citrate concentration should not be so great that it detrimentally affects the coagulation properties of blood, the concentration of citrate should be sufficiently high that it will be effective to achieve and maintain the pH of the final dialysate composition at a physiologically-acceptable pH. Typically, a citrate concentration that is one-quarter or less of the amount needed to achieve anti-coagulation can provide a dialysate composition with a physiologically-acceptable pH. Thus, the present dialysate precursor composition should have a minimum citrate concentration of about 20 mEq/L in order to provide the desired dialysate pH. In one embodiment, the dialysate precursor composition contains citrate at a concentration ranging from about 20 to about 900 mEq/L and in a preferred embodiment the composition contains citrate at a concentration ranging from about 70 to about 150 mEq/L.

Although citrate functions as an acidifying agent to lower the pH of a dialysate composition, in one aspect the present invention introduces a buffering anion to the dialysate precursor composition in order to maintain the pH of the final dialysate composition within a physiologically-acceptable range. As used herein, "buffering anion" refers to a physiologically acceptable anion that adjusts and regulates the pH of a composition. Suitable buffering anions include, for example, acetate, lactate, and mixtures thereof (i.e., acetate and/or lactate), which are compounds that will minimize changes in hydrogen ion concentration of a dialysate composition. As used herein, the phrase "lactate and/or acetate" means that either lactate alone, acetate alone, or a mixture of lactate and acetate may be used, or present, in the composition.

As used herein, "acetate" refers to an acetate anion, in any form, including acetic acid and salts of acetic acid. Acetate is an organic, monocarboxylate with the formula H₃C—COO⁻. The acetate salt is composed of one or more acetate anions in association with one or more physiologically-acceptable cations. Exemplary physiologically-acceptable cations include, but are not limited to, protons, ammonium cations and metal cations, where metal cations are preferred. Suitable metal cations include, but are not limited to, sodium, potassium, magnesium and calcium, where sodium and potassium are preferred, and sodium is more preferred.

Exemplary acetate compounds of the present invention include, but are not limited to, acetic acid, sodium acetate, sodium acetate trihydrate, potassium acetate, calcium acetate, calcium acetate monohydrate, magnesium acetate, and; magnesium acetate tetrahydrate. In one embodiment, the acetate of the dialysate precursor composition is present in the form of sodium acetate or potassium acetate, and in a preferred embodiment, acetate is in the form of sodium acetate.

As used herein, "lactate" refers to a lactate anion, in any form, including lactic acid and salts of lactic acid. Lactate is an organic, monocarboxylate with the formula H₃C—CH(OH)—COO⁻. A lactate salt is composed of one or more lactate anions in association with one or more physiologically-acceptable cations. Exemplary physiologically-acceptable cations include, but are not limited to, protons, ammonium cations and metal cations, where metal cations are preferred. Suitable metal cations include, but are not limited to, sodium, potassium, magnesium and calcium, where sodium and potassium are preferred, and sodium is more preferred.

Exemplary lactate compounds of the present invention include, but are not limited to, lactic acid, sodium lactate, potassium lactate, calcium lactate and magnesium lactate trihydrate. In one embodiment, the lactate of the dialysate precursor composition is present in the form of sodium lactate or potassium lactate, and most preferably lactate is in the form of sodium lactate.

In general, the dialysate precursor composition will typically contain more equivalents of citrate than equivalents of buffering anion. The precursor composition preferably contains more equivalents of citrate than equivalents of acetate, lactate, or lactate+acetate. In one embodiment, the dialysate precursor composition contains citrate at a concentration ranging from about 20 to about 900 mEq/L together with a buffering anion selected from acetate and/or lactate at a concentration ranging from about 0.01 to about 150 mEq/L. In a preferred embodiment the composition contains citrate from about 70 to about 150 mEq/L and a buffering anion selected from acetate and/or lactate at a concentration ranging from about 0.3 to about 125 mEq/L.

As the amount of citrate in the dialysate precursor composition is increased, it tends to lower the pH of the dialysate made with the precursor. With a lower dialysate pH, there is not as much need to buffer the precursor to ensure that the dialysate pH does not rise to a physiologically unacceptable level. Therefore, as a general rule, as higher equivalents of citrate are used in the dialysate precursor composition, less equivalents of buffering anion are required. Conversely, as less equivalents of citrate are used in the dialysate precursor composition, more equivalents of a buffering anion are required.

As used herein, the phrase "physiologically-acceptable cations" refers to cations normally found in the blood, plasma, or serum of a mammal, or cations that may be tolerated when introduced into a mammal. Suitable cations include protons, ammonium cations and metal cations. Suitable metal cations include, but are not limited to, the cationic forms of sodium, potassium, calcium, and magnesium, where sodium and potassium are preferred, and sodium is more preferred. An ammonium cation, i.e., a compound of the formula $R_4N^+$ where R is hydrogen or an organic group, may be used so long as it is physiologically acceptable. In a preferred embodiment, the cation is selected from hydrogen (i.e., proton), sodium, potassium, calcium, magnesium, and combinations thereof.

When the pH of a dialysate composition begins to increase (i.e., the dialysate becomes more basic) during the course of a dialysis treatment, the buffering anion, when present in an effective amount, prevents the pH of the dialysate composition from rising beyond a physiologically-acceptable range. For compositions having the citrate concentrations described above, and to provide the desired buffering effect, the precursor composition should contain from about 0.01 to about 150 mEq/L of buffering anion, preferably selected from acetate, lactate and mixtures thereof. In a preferred embodiment, the precursor composition contains from about 0.3 to about 125 mEq/L of acetate and/or lactate. In one embodiment, the buffering anion is a mixture of acetate and lactate. In another embodiment, the buffering anion is acetate, and lactate is not present in the composition. In another embodiment, the buffering anion is lactate, and acetate is not present in the composition.

With peritoneal dialysate, in order to facilitate the diffusion between blood and dialysate, it is desirable to maintain an osmotic gradient between the fluids by adding an osmotic agent to the dialysate. The presence of an osmotic agent in the peritoneal dialysate will encourage excess fluid and metabolic waste byproducts to flow from the blood and into the dialysate. A suitable osmotic agent for the precursor dialysate composition is sugar. The sugar is preferably selected from glucose (e.g., dextrose), poly(glucose) (i.e., a polymer made from repeating glucose residues, e.g., icodextrin, made from repeating dextrose units), or fructose. While it is possible to make a dialysate precursor with no sugar, if sugar is to be added to the dialysate composition, it is generally dextrose. It is further appreciated that any biocompatible, non-sugar osmotic agent that functions as an equivalent could be a viable substitute. The sugar is typically present in the dialysate precursor composition at a concentration of less than about 2,700 g/L.

A patient's blood serum contains several components including, for example, proteins, carbohydrates, nucleic acids, and various ions. Typically, a dialysate composition prescribed by a physician is chosen to reduce, increase, or normalize the concentration of a particular component in the serum. Several cations may be prescriptively included as part of the precursor dialysate composition. Suitable cations may include, for example, sodium, potassium, calcium and magnesium. In the dialysate precursor composition, the preferred concentration range for sodium is from about 2,000 to about 5,000 mEq/L. The preferred concentration range for potassium is less than about 250 mEq/L. The preferred concentration range for calcium is less than about 250 mEq/L. The preferred concentration range for magnesium is less than about 100 mEq/L. As used herein, a concentration of less that about a recited value includes zero.

As used herein, "mEq/L" refers to the concentration of a particular dialysate component (solute) present in proportion to the amount of water present. More specifically, mEq/L refers to the number of milli-equivalents of solute per liter of water. Milli-equivalents per liter are calculated by multiplying the moles per liter of solute by the number of charged species (groups) per molecule of solute, which is then multiplied by a factor of 1,000. As an example, when 10 grams of citric acid are added to a liter of water, the citric acid is present at a concentration of 10 g/L. Anhydrous citric acid has a molecular weight of 192.12 g/mol; therefore, the number of moles per liter of citric acid, and consequently citrate anion (since there is one mole of citrate anion per mole of citric acid), is 10 g/L divided by 192.12 g/mol, which is 0.05 mol/L. Citrate anion has three negatively charged species in the form of carboxylate groups. Accordingly, the citrate concentration of 0.05 mol/L is multiplied by three and then by 1,000, in order to provide a concentration of citrate in terms of mEq/L, which in the present example is 156 mEq/L of citrate anion.

A preferred water of the invention is treated in order that it is essentially pyrogen-free (i.e., is sterile) and at least meets the purity requirements established by the Association for the Advancement of Medical Instrumentation (AAMI) for dialysate compositions. The water may also be referred to as treated water or AAMI-quality water. A monograph describing water treatment for dialysate, monitoring of water treatment systems, and regulation of water treatment systems is available from AAMI (Standards Collection, Volume 3, Dialysis, Section 3.2 Water Quality for Dialysis, 3 ed., 1998, AAMI, 3330 Washington Boulevard, Arlington, Va. 22201) or through the Internet at http://www.aami.com. In addition, all of the other components of the precursor dialysate composition of the present invention are preferably at least United States Pharmacopeia (USP)-grade purity, which is generally a purity of about 95%. The purity of the components is preferably at least about 95%, more preferably at least about 98%, and more preferably at least about 99%.

The dialysate precursor composition of the present invention will typically have a pH ranging from about 1 to about 6.5, more typically from about 1 to about 4, more typically from about 2 to about 4, at a temperature of about 15° C. to about 40° C., before dilution with treated water and base to afford the dialysate composition.

In a preferred embodiment, the dialysate precursor composition contains components including chloride at a concentration ranging from about 2,000 to about 5,000 mEq/L; citrate at a concentration ranging from about 70 to about 150 mEq/L; acetate and/or lactate at a total concentration ranging from about 0.3 to about 125 mEq/L; at least one physiologically-acceptable cation selected from hydrogen, sodium at a concentration ranging from about 2,000 to about 5,000 mEq/L, potassium at a concentration of less than about 250 mEq/L, calcium at a concentration of less than about 250 mEq/L, and magnesium at a concentration of less than about 100 mEq/L; and glucose (preferably dextrose) at a concentration of less than about 2,700 g/L, where the composition meets or exceeds the AAMI standard set for dialysate. In one embodiment, the above-listed ingredients are the only active ingredients in the composition.

The present invention provides a method of forming the precursor dialysate composition as described above. In this method, ingredients are mixed together so as to provide the dialysate precursor composition. Thus, a source of chloride, a source of citrate, and a source(s) of buffering anion (e.g., acetate and/or lactate) are mixed together with treated water, in amounts which ultimately provide the desired concentration of each, as set forth above. Suitable sources for these ingredients are well known in the art. Indeed, the chemical characteristics for the compounds used in the present invention, such as molecular weight and solubility, are available in the art such that one of ordinary skill in the art will know how to prepare the composition of the present invention. See, e.g., the Sigma and Aldrich catalogs from Sigma-Aldrich (Milwaukee, Wis.; http://www.sial.com).

For example, the chloride source may be any of hydrochloric acid, sodium chloride, potassium chloride, magnesium chloride, ammonium chloride, or the like. The citrate source may be any of citric acid, sodium dihydrogen citrate, disodium hydrogen citrate, trisodium citrate, trisodium citrate dihydrate, potassium dihydrogen citrate, dipotassium hydrogen citrate, calcium citrate, magnesium citrate, or the like. The acetate source may be any of acetic acid, sodium acetate, sodium acetate trihydrate, potassium acetate, calcium acetate, calcium acetate monohydrate, magnesium acetate, magnesium acetate tetrahydrate, and the like. The lactate source may be any of lactic acid, sodium lactate, potassium lactate, calcium lactate, magnesium lactate trihydrate, and the like. Any or all of these chemicals are commercially available, in USP-grade if desired, from many chemical supply houses including, for example, Aldrich Chemical Co., Milwaukee Wis. The treated water may be obtained by following standard purification techniques, including, for example, distillation and reverse osmosis. Alternatively, the treated water may be purchased commercially. Such treated water is used in all, or nearly all, dialysis clinics and accordingly is well known to one of ordinary skill in the art.

In one embodiment, the invention provides a method of forming a dialysate precursor composition which includes the step of mixing water, chloride, citrate, at least one buffering anion selected from acetate and/or lactate, and at least one physiologically-acceptable cation, to provide a composition having chloride at a concentration ranging from about 1,000 to 7,000 mEq/L, citrate at a concentration ranging from about 20 to 900 mEq/L, and at least one buffering anion selected from acetate and/or lactate at a total concentration ranging from about 0.01 to 150 mEq/L.

In a preferred embodiment, sources of water, chloride, citrate, acetate and physiologically-acceptable cations are mixed so as to provide a composition having water, chloride at a concentration ranging from about 2,000 to about 5,000 mEq/L; citrate at a concentration ranging from about 70 to about 150 mEq/L; acetate at a concentration ranging from about 0.3 to about 125 mEq/L; at least one physiologically-acceptable cation selected from hydrogen, sodium at a concentration ranging from about 2,000 to about 5,000 mEq/L, potassium at a concentration of less than about 250 mEq/L, calcium at a concentration of less than about 250 mEq/L, magnesium at a concentration of less than about 100 mEq/L; and glucose at a concentration of less than about 2,700 g/L, where the composition meets or exceeds the AAMI-quality standard set for dialysate.

In another aspect, the present invention provides a dialysate composition. The dialysate composition is preferably prepared from the dialysate precursor composition described above by adding treated water and a base, preferably bicarbonate, to the precursor composition. Upon the addition of base and water, the dialysate precursor composition provides a composition suitable for performing dialysis.

For example, bicarbonate concentrate, or diluted bicarbonate concentrate, may be added to the dialysate precursor composition, or diluted dialysate precursor composition, to provide a dialysate composition according to the present invention. Typically, one volume part of dialysate precursor composition is diluted with between 33 and 45 parts of diluted base concentrate, to provide the dialysate composition. The dialysate precursor will contain citrate (as the primary acidic ingredient of the acid concentrate), bicarbonate (as the primary basic ingredient of the base concentrate) and buffering anion preferably selected from acetate and/or lactate.

In one embodiment, the dialysate composition contains ingredients including treated water; chloride at a concentration ranging from about 20 to about 200 mEq/L; citrate at a concentration ranging from about 0.5 to about 30 mEq/L; at least one buffering anion selected from acetate and/or lactate at a concentration ranging from about 0.01 to about 4.5 mEq/L; bicarbonate; and at least one physiologically-acceptable cation.

In one embodiment, the dialysate composition includes one or more sugars selected from glucose (preferably dextrose), poly(glucose) (preferably, poly(dextrose), e.g., icodextrin), and fructose at a concentration of less than about 45 g/L. Instead, or in addition to sugar, the dialysate composition may contain one or more 25 amino acids. Preferably, the dialysate composition contains water that meets or exceeds the purity requirements established by AAMI for dialysate and all other components have at least USP-grade purity. In another preferred embodiment, the dialysate composition has a pH of about 5 to about 8.5 at a temperature of about 25° C. to about 40° C., and more typically has a pH of about 6.4 and 7.6 at this temperature range, and preferably has a pH of about 7.2 to about 7.4.

In other embodiments, the dialysate composition contains ingredients including water, chloride at a concentration ranging from about 40 to about 150 (more preferably, from about 60 to about 120) mEq/L; citrate at a concentration ranging from about 1.5 to about 4.5 (more preferably, from about 2 to about 3) mEq/L; acetate and/or lactate at a total concentration ranging from about 0.01 to about 4.0 (more preferably, from about 0.2 to 0.5) mEq/L; bicarbonate at a concentration ranging from about 25 to about 45 mEq/L; at least one physiologically-acceptable cation selected from hydrogen, sodium at a concentration ranging from about 60 to about 190 (more preferably, from about 70 to about 150) mEq/L, potassium at a concentration of less than about 5 mEq/L, calcium at a concentration of less than about 5 mEq/L, and magnesium at a concentration of less than about 2 mEq/L; and glucose (preferably, dextrose) at a concentration of less than about 45 (preferably, less than about 8) g/L, where the combined composition meets or exceeds the AAMI-quality standard set for dialysate.

In another aspect, the present invention provides a method of forming a dialysate composition. In a preferred embodiment, the method includes combining the dialysate precursor composition, as described above, with a base concentrate, perferably a bicarbonate base concentrate, and treated water as needed to provide prescribed concentrations of solutes in the dialysate. The base concentrate contains water, bicarbonate, and has a pH of greater than 7. The pH will be greater than 7 because of the presence, in the concentrate, of one or more "bases." Base concentrate is currently used in most dialysis clinics. The base in a typical base concentrate is bicarbonate, also known as hydrogen carbonate, having the chemical formula $HCO_3$. Bicarbonate carries a net negative charge, and accordingly will be associated with a positively charged species. Suitable positively charged species include physiologically-acceptable metal cations such as the cationic forms of sodium, potassium, calcium and magnesium.

The base from which base concentrate is almost universally prepared in dialysis clinics is sodium bicarbonate, and this is the preferred base in the present compositions and methods. The bicarbonate concentrate in a dialysate is preferably from about 25 to 40 mEq/L. Acetate base is not a preferred base.

Optionally, the sodium bicarbonate in a base concentrate may be replaced, in part, with a different physiologically-acceptable base. The anionic portion of a suitable replacement for sodium bicarbonate may be, for example, carbonate, lactate, citrate and acetate. Accordingly, the base for a base concentrate may be selected from the salt forms of any of bicarbonate and, optionally, carbonate, lactate, citrate and acetate. Also present in the salt forms will be one or more physiologically-acceptable cations selected from sodium, potassium, calcium and magnesium. These salts and acids are electronically neutral, i.e., there are an equal number of negative and positive charges.

Preferably, the dialysate precursor composition and the base concentrate are mixed so as to arrive at a dialysate composition that contains ingredients including water, chloride at a concentration ranging from about 40 to about 150 (more preferably, from about 60 to about 120) mEq/L; citrate at a concentration ranging from about 1.5 to about 4.5 (more preferably, from about 2 to about 3) mEq/L; acetate and/or lactate at a total concentration ranging from about 0.01 to about 4.0 (more preferably, from about 0.2 to 0.5)

mEq/L; bicarbonate at a concentration ranging from about 25 to about 45 mEq/L; at least one physiologically-acceptable cation selected from hydrogen, sodium at a concentration ranging from about 60 to about 190 (more preferably, from about 70 to about 150) mEq/L, potassium at a concentration of less than about 5 mEq/L, calcium at a concentration of less than about 5 mEq/L, and magnesium at a concentration of less than about 2 mEq/L; and glucose (preferably, dextrose) at a concentration of less than about 45 (preferably, less than about 8) g/L, where the combined composition meets or exceeds the AAMI-quality standard set for dialysate. Higher concentrations of citrate could typically be used when a patient is simultaneously infused with excess calcium.

In dialysate compositions of the invention, the citrate-containing dialysate precursor composition is combined with the base concentrate so as to arrive a at final dialysate composition having a pH in the physiological range of 5 to 8.5, and preferably from about 7.2 to about 7.4.

In another aspect, the present invention provides an aqueous acid-concentrate composition useful in hemodialysis that contains, at a minimum, water, chloride, citrate, and cations to provide for a neutral (i.e., no net charge) composition, but does not contain any of bicarbonate, acetate or lactate. The water is "treated water" as defined herein, or a water of even greater purity, and each of the chloride and citrate is USP-grade quality or better (for example, reagent grade, preferably of at least 99% purity).

The aqueous acid-concentrate composition contains chloride at a concentration of about 1,000 to about 7,000, preferably of from about 2,000 to about 5,000 mEq/L; citrate at a concentration ranging from about 20 to about 200, preferably from about 70 to about 150 mEq/L; and sufficient physiologically-acceptable cations to provide for a neutral (i.e., no net charge) composition, where the composition has a pH of less than 4, preferably between about 2 and about 3, and more preferably about 2.2 to 2.8, and does not contain any of bicarbonate, acetate, or lactate.

Although this aqueous acid-concentrate composition does not contain any of bicarbonate, acetate or lactate, it is still usefully employed in dialysate manufacture. For instance, it provides a convenient stock solution to which may be added bases and/or salts. Since it is a liquid, it is conveniently employed as the acid concentrate in traditional dialyzers that employ the three-stream proportionate pumping mechanism for making dialysate. Care should, however, be taken when combining base, such as bicarbonate, with the aqueous acid-concentrate composition, in order that the desired pH of the final dialysate is obtained.

In a related embodiment, the invention provides a method of preparing dialysate, wherein a basic solution containing water and at least one of bicarbonate, carbonate, acetate, lactate, and citrate having a pH of greater than 7 is mixed with the aqueous acid-concentrate composition described above, i.e., an acidic solution having a pH of less than 4 containing, at a minimum, chloride, citrate, and cations, the cations providing for an electronically neutral composition, where this acidic solution does not contain any of bicarbonate, acetate or lactate. According to this method, the relative amounts of basic and acidic solutions that are combined should be carefully tailored so as to achieve a desired dialysate pH, at all times throughout a dialysis treatment session. Typically, that desired dialysate pH is within the range of 6.8 to 7.8.

While citric acid-containing hemodialysate compositions are known in the art, see U.S. Pat. No. 5,252,213 of Ahmad et al., such compositions are disclosed as dry pellets (or other like solid form) which are dissolved in water to provide the hemodialysate composition. Those compositions provide a convenient source of all of the components of a hemodialysate composition, and are intended to be combined with water and essentially no other ingredients, before being used in a hemodialysis treatment. Thus, each pellet contains both the acidic and basic components of a hemodialysate composition which ensures the pH of the resulting hemodialysate.

The present invention makes an aqueous acid concentrate that may be used in the preparation of either hemodialysate or peritoneal dialysate. The citric acid concentrate is intended to be combined with treated water and base concentrate, as is currently the practice in dialysis clinics, so as to afford the dialysate composition. In clinics, the pH of the base concentrate, which typically contains sodium bicarbonate, can vary widely and affect the resulting dialysate pH. Therefore, when using a citric acid-containing acid concentrate in the manner according to the present invention, the concentrate should contain a buffering agent in order to maintain the resulting dialysate pH within a pre-determined, physiologically-acceptable range throughout the duration of the dialysis treatment. Buffering is required because increasing the amount of citric acid to lower the dialysate pH may cause a significant decrease in serum calcium concentration. This need for a buffer with citric acid concentrate is a departure from the practice in the art.

Most dialysates in use today use acetic acid as the acidifying agent to keep the pH of the final dialysate within an acceptable physiological range. As noted above, the 'acid concentrate' that is used in most hemodialysis treatments today is shipped as a liquid. The concentrate is in liquid form because acetic acid is a liquid acid. Although this solution is far more concentrated than the final dialysate which is actually used to purify a patient's blood (it can be as much as 45 times more concentrated), still three-quarters of its weight and volume is water. The present invention utilizes citric acid, rather than acetic acid, as the main acidic material in an acid concentrate.

In an acid concentrate that contains citrate, the citrate will be primarily in the form of citric acid. There are certain ramifications of, using citric acid in an acid concentrate for dialysate. For example, citric acid forms citrate in the blood which binds with free magnesium and calcium. In fact, the strong binding of calcium with citrate is used by blood banks to prevent clotting in donated blood. While the level of citric acid used in the dialysate of the present invention is only a fraction (less than one-quarter) of the amount needed to achieve measurable anticoagulation, medical prudence dictates using the least amount of citric acid possible in a dialysate in order to minimize undesired calcium binding in the blood. When dialysate is prepared from 45× dilution of precursor dialysate, and the precursor dialysate has citrate concentrations within the range of 200–900 mEq/L, then the precursor preferably has elevated levels of calcium and/or magnesium to compensate for the extent to which citrate will bind serum calcium and magnesium.

The amount of citrate present in the acid concentrate of the invention should be the least amount necessary to achieve a final dialysate pH within the range of 7.2 to 7.4. We have found that using about 7 grams citric acid per liter of water in an acid concentrate (providing a concentration equal to 2.4 mEq/L) would minimize the calcium binding and achieve an acceptable dialysate pH.

However, the use of citrate in an acid concentrate led to an intermittent problem when the dialysate was used in a clinical setting. Generally, late in a dialysis session (usually in the last hour of treatment) some dialysis machines would sound an alarm due to high pH. This problem was traced to the base solution.

Bicarbonate is the basic material present in most base solutions. In most dialysis clinics, the bicarbonate solution is made by the clinic staff just before use. The procedure often can involve pouring a pre-determined amount of sodium bicarbonate (typically one package) into a jug, adding a measured amount of water and manually mixing (usually by shaking the container). Any, some, or all of the following factors may cause variations in the pH of the bicarbonate from the expected standard: the amount of water added can be more or less than specified, the mixing can be insufficient to thoroughly put all the sodium bicarbonate powder into solution, the container could be left sitting for a period before use, or the patient has a long dialysis treatment.

When carefully measuring and adequately mixing the bicarbonate, the pH of the concentrated solution was 7.85 (±0.05). However, in practice, samples of bicarbonate concentrate that are prepared by clinic staff had a range of pH values from 7.78 to 8.13. Furthermore, the pH of the residual bicarbonate concentrates that had just been used for a hemodialysis treatment were found to range from 7.9 to 8.24. We speculate that this variation in pH, most noticeably observed in the 'spent' dialysate, may be from any one of, or a combination of, the following factors:

Insufficient water was added to the base concentrate, causing a higher than desired concentration of bicarbonate.

Inadequate mixing of the powder and water, allowing some settling of the powder and therefore a more concentrated bicarbonate solution and rising pH late in the dialysis treatment (at which time the powder has completely dissolved).

The bicarbonate concentrate releases carbon dioxide over time, thereby causing slowly increasing pH.

One way to ensure against the pH rising to the alarm threshold during a dialysis treatment is to increase the amount of acid used, which causes a more acidic dialysate. However, increasing the amount of citric acid also increases the amount of calcium binding—accordingly, this approach must be used with caution. An alternative approach taken according to the present invention is to mitigate the effects of an increase in dialysate pH which is caused by a rising pH of the bicarbonate concentrate, through inclusion of a buffering agent in the acid concentrate.

Acetate and/or lactate were selected as the preferred buffering agents in the present invention. Each of these anions is found naturally in the blood of dialysis patients. Sodium acetate is a preferred buffer because it contains the same ingredients, sodium and acetate, that are in virtually all current dialysates (provided from the sodium chloride and acetic acid).

Surprisingly, there is not a linear relationship between the amount of sodium acetate buffer present in the acid concentrate and the pH of the final dialysate solution. It might be expected that adding increasing amounts of this acidic buffer to an acid concentrate would cause a linear decrease in the pH of the final solution. However, this is not the case. Within a narrow range the sodium acetate causes a significant decrease in the pH of the dialysate. However, this buffering action of the sodium acetate is only observed when the pH of the bicarbonate concentrate exceeds 8.0. At higher pH values of the bicarbonate concentrate, the buffering action of the acetate is more apparent.

This effect is shown in the FIGURE. The chart of the FIGURE illustrates the resulting dialysate pH obtained using a relatively high bicarbonate concentration at pH 8.14 combined with treated water and the present invention's dialysate precursor using 2.4 mEq/L of citrate and increasing the sodium acetate concentration from 0 to 3.5 grams per liter. As shown in the FIGURE, increasing the concentration of sodium acetate beyond a certain point does not increase the sodium acetate's buffering action nor does it make the buffering action apparent at lower values of bicarbonate pH. While not wishing to be bound by theory, the following is suggested to explain the surprising effect of using acetate in the acid concentrates of the invention.

Citric acid is a multi-protic acid. It contains three labile hydrogen atoms that can contribute to the acidity of a solution. There is a separate equilibrium associated with the liberation of each hydrogen ion:

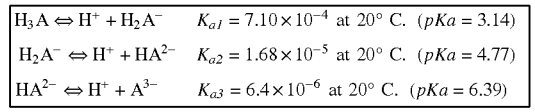

where A represents the citrate anion. At a pH greater than 7 almost all of the citric acid is dissociated and the predominant species are $H^+$ and $A^{3-}$.

Acetic acid is a monoprotic acid, i.e., it contributes only one labile hydrogen atom to the solution and there is only one equilibrium constant for the equilibrium:

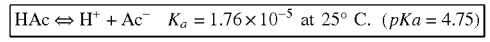

where Ac represents the acetate anion. When sodium acetate (NaAc) is introduced to aqueous solution it dissolves completely into sodium ions ($Na^+$) and acetate ions ($Ac^-$). The sodium is considered to be a 'spectator' ion—it does not participate in any equilibria. The acetate ($Ac^-$) anion undergoes hydrolysis:

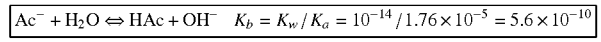

A buffer is a solution whose composition is designed to resist changes in pH. Small amounts of acid or base can be added to a buffer and the pH will change very little. These statements imply that the buffer solutions are able to react with both $H^+$ (also commonly written as $H_3O^-$) and $OH^-$ ions. Two common kinds of buffer solutions are ones which contain (1) a weak acid plus a salt of the weak acid, and (2) a weak base and a salt of the weak base. A less common type contains a weak acid (e.g., citric acid) and a salt of another weak acid (e.g., sodium acetate which is derived from acetic acid).

For simple aqueous solutions, the buffering action can often be calculated based on available data, specifically: concentration of acid, concentration of salts, temperature, and appropriate equilibrium constants, $K_i$. The situation with the acid concentrates and dialysates of the present invention is more complex. Additional equilibria are introduced by the addition of calcium (Ca) and magnesium (Mg) to the dialysate. These metal ions have their own equilibria with carbonate, acetate, and citrate ions. Equilibrium constants $K_i$, for some of the equilibria are not available and so their impact on the pH of a dialysate formulation cannot be absolutely predicted. Direct measurement of solution pH by titrimetric methods may be used in the formulation of the dialysate. The predominant equilibria in solution are given by (not an exhaustive list):

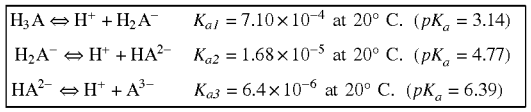

where A represents the citrate anion.

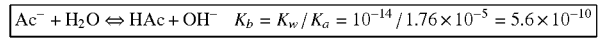

where Ac represents the acetate anion.

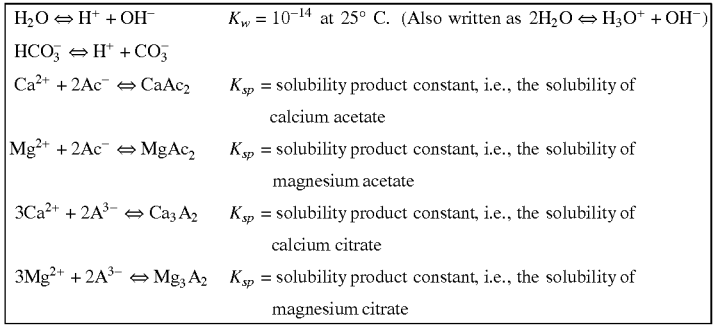

Since the $A^{3-}$ species predominates at a pH above 7.0, the calcium and magnesium equilibria with lower citrate ions ($HA^{2-}$ and $H_2A^-$) are not considered.

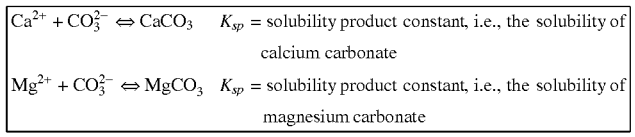

If all of the constants and concentrations were known for 37° C., then the above equations could be set into a matrix and the pH and buffering action could be obtained by calculation. The situation is further restrained by the requirement to keep the pH within a physiological range (especially near the end of dialysis when the pH of the bicarbonate concentrate tends to rise). Normally, this could be accomplished with the addition of more (citric) acid, however, this is precluded by the need to keep the concentration of citrate ions (from citric acid) as low as possible. As discussed below, this is required because of the tendency of calcium and magnesium to combine with citrate ions thus lowering the serum levels of calcium and magnesium to clinically unacceptable levels. The solution to this problem is found in Applicants' selection of the buffer.

Sodium citrate is not used in the buffer because of the aforementioned need to maintain an acceptably low total citrate ion concentration. Acetate or lactate may be used because of (1) their appropriate buffering action, (2) cost, (3) acetate ions (which are preferred) are already used (from acetic acid) in dialysate formulations and thus no new variable is introduced to the chemistry of the dialysate.

The buffering action manifests itself by lowering the pH of the dialysate to physiological, non-alarm levels when the pH of the bicarbonate is high—either from incorrect mixing or the passage of time since mixing. When the bicarbonate pH is appropriate, the buffer is present, but it is transparent to the operation of the dialysate. When bicarbonate concentrate solutions were used with a pH of <8.0 the buffering action was not apparent. When bicarbonate concentrate solutions of 8.1<pH<8.3 were used, the buffering action was evident (see FIGURE). The buffering action is particularly evident for sodium acetate concentrations between 0.5 and 3.0 g per liter of acid concentrate, where this is a preferred range for the acid concentrates of the present invention.

In another aspect, the present invention provides citrate-containing compositions particularly suitable for peritoneal dialysis (PD). These composition may be in either solid or liquid form, i.e., either a mixture of dry ingredients, which is a precursor to the peritoneal dialysate, or a solution of various solutes, which itself is a peritoneal dialysate. The mixture of dry ingredients contains, at a minimum, chloride, citrate, bicarbonate and dextrose, along with one or more cationic species that provide a neutral (i.e., no net charge) composition. The solution form of the PD composition contains, at a minimum, water in addition to the above-listed minimum ingredients required for the dry composition. Whether in solid or liquid form, the citrate acid-containing compositions suitable for peritoneal dialysis are sterile.

The peritoneal dialysate of the present invention (i.e., the PD solution dialysate) contains water in addition to the following ingredients, in the indicated amounts, where the amounts are expressed in terms of mEq per liter of the PD solution: citrate (0.5–6, preferably 1.5–4.5, more preferably 2–3); chloride (20–200, preferably 40–150, more preferably 60–120); and bicarbonate (5–100, preferably 10–70, more preferably 30–40). In addition, the solution form of the PD composition contains glucose at a concentration, in terms of g per liter of the solution form, of 10–100, preferably 20–80, more preferably 40–60. In addition, the solution form of the PD composition contains a sufficient number of physiologically-acceptable cations to neutralize all of the citrate, chloride, bicarbonate, and any other anionic species that may be present in the composition. This PD solution dialysate is sterile, as required for all dialysates approved for peritoneal dialysis by the U.S. Food & Drug Administration.

In a preferred embodiment, the solution form of the PD composition contains acetate and/or lactate, where in total these two anions are present in an amount, expressed in terms of mEq per liter of PD solution, of 0.01–10, preferably 0.1–1, more preferably 0.25–0.75. The cationic species present in the PD solution are essentially within the same concentration ranges as previously set forth herein for cationic species (i.e., sodium, magnesium, calcium and potassium) in the hemodialysis compositions.

The present invention provides a dry composition which, upon combination with sterile water, will generate the above-described PD solution dialysate. This dry composition is, itself, sterile. According to one approach, such a dry composition can be described in terms of grams of a specific ingredients per each (one) gram of citrate. Using these terms, the dry composition contains chloride in an amount of 5–50, preferably 10–40, more preferably 20–30; bicarbonate in an amount of 1–50; preferably 5–30, more preferably 10–20; and glucose in an amount of 100–600; preferably 150–500, more preferably 200–350, where each of these values are grams per 1 gram of citrate. In calculating these amounts, the formula weights for citrate, chloride, and bicarbonate are 189.1 g/mol, 35.5 g/mol and 61.0 g/mol, respectively, where each of chloride and bicarbonate carry a single charge, while citrate carries a triple charge. The dry PD composition contains sufficient cationic species to provide a neutral (no net charge) composition. In addition, the pH of the resulting solution will be within a physiologically tolerable range, preferably within the range 6.4–7.6.

According to another approach, the content of the dry PD composition can be described in terms of the number of milli-equivalents of a specific charged species present in the composition per each (one) milli-equivalent of citrate present in the composition. In these terms, the dry composition contains chloride in an amount ranging from 1–200, preferably 10–100, more preferably 30–50 mEq; and bicarbonate in an amount ranging from 1–50, preferably 5–30; more preferably 10–20 mEq. In addition, the dry PD composition contains glucose in an amount of 100–600; preferably 150–400, more preferably 200–300, where each of these values are grams per 1 gram of citrate.

Both the peritoneal dialysate and the dry precursor thereto are necessarily sterile in order to be useful in peritoneal dialysis. Accordingly, the preparation of each is necessarily conducted under sterile conditions, and/or the resulting composition is rendered sterile by appropriate sterilizing treatment. According to one embodiment, the dry PD composition is prepared by combining sodium chloride (5.67 g), calcium chloride dihydrate (0.26 g), magnesium chloride hexahydrate (0.10 g) sodium bicarbonate (2.94 g), anhydrous citric acid (0.15 g), sodium acetate trihydrate (0.041 g) and dextrose (42.5 g), where each of the listed chemicals is in sterile form, and the combining procedure is conducted in a sterile environment; This dry composition contains 0.15 g citrate, 3.6 g chloride, 2.1 g bicarbonate and 42.5 g glucose which, in terms of each gram of citrate, is 24 g chloride, 14 g bicarbonate and 283 g dextrose, and in terms of each milli-equivalent of citrate is 42 mEq chloride and 14.5 mEq bicarbonate.

The dry PD composition, and the peritoneal dialysate prepared therefrom, is described in terms of anionic species because each anionic species may be introduced into the composition in any dry form that is physiologically acceptable and contains the anionic species of interest. Thus, for example, "citrate" can be introduced into the dry composition in any dry form that contains citrate. Examples are citric acid (anhydrous), citric acid monohydrate, trisodium citrate, citric acid disodium salt sesquihydrate, citric acid monosodium salt, citric acid tripotassium salt monohydrate, etc.

Likewise, each of the bicarbonate and chloride may be introduced simultaneous with cations selected from sodium, potassium, magnesium and calcium, and may be in anhydrous or hydrate forms. Accordingly, the dry composition is described in terms of "chloride", "citrate", and "bicarbonate", rather than specifying any particular salt or protonated form thereof.

The chloride is present in the dry composition in the form of a salt. Suitable chloride salts include, without limitation, sodium chloride, potassium chloride, calcium chloride, and magnesium chloride. A preferred chloride salt is sodium chloride.

The citrate is present in the dry composition in form of an acid and/or a salt. Citric acid is a suitable acid form of citrate. Trisodium citrate, tripotassium citrate, and calcium citrate (i.e., tricalcium dicitrate) are all suitable salt forms of citrate. The citrate may be in a mixed acid/salt form, i.e., complexed simultaneously to one or more protons and one or more metal cations. Typical examples of citrate in mixed acid/salt form include, without limitation, potassium dihydrogen citrate, dipotassium hydrogen citrate, and disodium hydrogen citrate. A preferred citrate is citric acid.

The bicarbonate is present in the dry composition in the form of a salt. Suitable bicarbonate salts include, without limitation, sodium bicarbonate, and potassium bicarbonate. A preferred bicarbonate salt is sodium bicarbonate.

Glucose is a component of most of the currently used peritoneal dialysates, and is incorporated into the peritoneal dialysate (and precursor thereto) of the present invention in order to provide the benefits that glucose is known to provide to peritoneal dialysates. For example, glucose is primarily useful as an osmotic agent, as discussed previously, and is also recognized to mitigate some of the undesirable side-effects of peritoneal dialysis. The glucose may also provide some nutritional supplement to the subject undergoing to the dialysis treatment. The most typical glucose isomer currently used in peritoneal dialysate is dextrose, i.e., α-D-glucose. This is a commonly known material of commerce, and is available in both hydrated and anhydrous forms. Either form may be used in the present PD composition.

Although the dry composition will be dry to the touch, it may contain some water. For instance, several of the salts and acids mentioned above as suitable ingredients for the dry PD composition are commonly available in hydrated form. Such hydrated forms are suitably used in preparing the dry PD composition provided herein. Each of the above-mentioned ingredients of the dry PD composition are available from many commercial supply houses. See, e.g., Sigma-Aldrich (http://www.sail.com). Preferably, the ingredients are of United States Pharmacopeia (USP)-grade purity or higher, which is generally recognized as a purity of at least about 95%.

Optional ingredients may be present in the dry PD composition. Suitable optional ingredients include, without limitation, amino acids.

The dry PD composition is readily prepared simply by mixing together weighed quantities of the various dry sterile ingredients under sterile conditions. Mixing is readily accomplished by agitating a combination of the ingredients until a homogeneous mixture results. The pre-weighed dry mixture may be packaged in hermetically-sealed packages for convenience in shipping, and to allow a technician to more easily prepare a solution form of the dry composition.

The dry dialysate powder technology of the present invention allows the preparation of peritoneal dialysate. This aspect of the invention creates a unique peritoneal dialysate using, in a preferred embodiment, citric acid as the acidifier, dextrose at concentrations exceeding 2.0% and bicarbonate as the basic anion. Other ingredients would include water as well as chloride, sodium, potassium, magnesium, and calcium, which could all be included at the concentration ranges specified for hemodialysis dialysate. Peritoneal dialysate would require no precursor (other than the dry powder) since the volumes of dialysate used per treatment are just a small fraction of the amounts used in hemodialysis. Making the peritoneal dialysate just prior to use (i.e., by adding sterile water to the sterile dry PD powder) would allow the use of bicarbonate as the basic anion. Normally, bicarbonate cannot be used in PD because solutions of it with citric acid do not have sufficient long-term stability to permit storage. To overcome this stability problem, currently used PD compositions typically contain lactate (rather than bicarbonate) as the basic anion. However, some health care professions prefer bicarbonate as the basic anion, and the present invention addresses that need.

The precise order in which the sterile water and dry ingredients are combined is unimportant. As one option, sterile water may be added to the dry PD composition described above. As another option, a desired volume of sterile water may be provided, and to this may be added each of the various other (sterile) ingredients of the solution PD composition. Typically, the final solution should be stirred or otherwise agitated, e.g., shaken, to form a homogeneous composition. "Handbook of Dialysis" $2^{nd}$ Ed. Dangirdas, J. T. and Ing T. S., eds. (Little, Brown, Boston, 1994) provides an extensive discussion of peritoneal dialysis (as well as hemodialysis).

PHYSIOLOGICAL EFFECTS

Citric acid was identified as a potential acidifying agent for dialysate because it is an inexpensive physiological acid. In addition, it has an extensive history of use in blood banks and also has been successfully used for regional anticoagulation in hemodialysis. Both these prior uses are based on the calcium binding effect of the citric acid. It is empirically observed that blood will coagulate if the concentration of free calcium in the blood is above a certain critical concentration. As citric acid is added to blood, the citrate binds with the free calcium and reduces its concentration. When the free calcium concentration is reduced to a certain point, the blood will no longer coagulate.

In the present invention, citric acid is employed in, dialysate as an acidifying agent to reduce the pH of the dialysate. However, using more than about 2.4 mEq/L of citric acid in dialysate may cause a significant decrease in serum calcium concentration, which may be clinically undesirable. At the level of 2.4 mEq/L of citric acid in dialysate, the increase in blood citrate concentration is typically small enough to not cause any noticeable detrimental effect on the coagulation behavior of blood. Indeed, there is typically no measurable increase in a patient's clotting time beyond that already achieved with their normal anticoagulation medicine, heparin.

Generally, kidney failure patients suffer from chronic acidosis. Their kidneys cannot rid the body of the H+ ions produced during normal metabolism. As a consequence, their bodies use excessive amounts of bicarbonate to buffer excess H+ ions. Because of the constant use of bicarbonate to neutralize acid, these patients have lower than normal levels of bicarbonate (carbon dioxide) when they arrive for their dialysis treatment. Traditionally, dialysis treatment seeks to correct an acidosis problem by using dialysate that contains higher than normal serum concentrations of bicarbonate. Thus, during treatment, the blood bicarbonate increases because of diffusion of some of this excess bicarbonate into the blood which helps restore total body bicarbonate. However, the traditional dialysis with a dialysate bicarbonate concentration of about 37 mEq/L is often not enough to maintain normal blood bicarbonate between dialysis sessions. Consequently, by the time the patient comes for the next dialysis session, the blood bicarbonate is again subnormal. The buffered citrate dialysate(s) of the present invention have shown some effect at replenishing the body's bicarbonate levels, thus helping to treat chronic acidosis.

The following examples are provided for purposes of illustration, not limitation.

EXAMPLES

Example 1

Acid Concentrate Formulation

The following amounts of the indicated USP-grade chemicals were carefully weighed out: 262.0 g sodium chloride (FW 58.45), 9.70 g calcium chloride (dihydrate, FW 147.02), 3.40 g magnesium chloride (hexahydrate, FW 203.3), 90.0 g dextrose (FW 180.16), 7.0 g citric acid (anhydrous, FW 192.12) and 1.75 g of sodium acetate (trihydrate, FW 136.08). The chemicals were placed in a large calibrated beaker and AAMI quality water was added to the 900 ml mark. The beaker was placed on a stirring plate and a stirring bar was used to agitated the chemicals and water. After approximately 10 minutes of stirring, the chemicals had completely dissolved and the solution was 'crystal clear.' The stirring bar was removed and the solution was 'topped off' with additional AAMI quality water to the 1 liter mark on the beaker. The stirring bar was reintroduced and the solution was stirred for another 3 minutes.

Example 2

Hemodialysis

The beaker of solution as prepared in Example 1 was taken to a Fresenius hemodialysis machine that was ready for use in testing (bypass) mode. In this configuration the machine makes dialysate in the same manner as when a patient is undergoing a dialysis treatment. The treated water supply line was attached to the machine and a container of bicarbonate concentrate was carefully prepared. All solutions were then attached to the machine and it was turned on.

The machine was allowed to run for 10 minutes at a dialysate flow rate of 800 ml/min. to ensure the prepared solutions had thoroughly filled their appropriate pathways through the machine. Additionally, both the machine's conductivity meter as well as an additional conductivity monitor that had been attached to the dialysate outflow line were monitored, with readings found to stay within the acceptable range (between 1310 and 1330 millisiemens). The pH of the machine-mixed dialysate was monitored by sampling the drain tube outflow at several intervals which averaged 1.0 minutes apart. The pH was 7.4, which was within the target range of 7.3 to 7.5. A sample of the outflow was analyzed at the University of Washington Medical Center's laboratory to confirm that the concentrations in the final dialysate were all within acceptable ranges for hemodialysis.

Finally, after receiving the appropriate approvals, the dialysate precursor and the resulting dialysate produced by the hemodialysis machine were repeatedly tested in actual patient treatments during clinical trials of the new dialysate. Throughout the trials, even with dialysis sessions lasting up to five hours, there were no instances of pH alarms noted.

Example 3

Dialysate Composition

One liter of dialysate composition, excluding sodium bicarbonate, in mEq/L, contains: sodium, 100.3; chloride, 104.25; calcium, 2.5; potassium, 1.0; magnesium, 0.75; acetate, 0.3; citric acid, 2.4; and, in g/l, dextrose, 2.0. The total chemical composition of this dialysate composition (which did not contain sodium bicarbonate) was (in grams): NaCl (5.822); CaCl$_2$ 2H$_2$O (0.139); KCl (0.074); MgCl$_2$ 6H$_2$O (0.036); NaC$_2$H$_3$O$_2$ (0.039); C$_6$H$_8$O$_7$ (0.155) and C$_6$H$_{12}$O$_6$ H$_2$O (2).

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A precursor composition for preparing a buffered dialysate, the precursor composition having a pH of 1–4 and comprising citrate at a concentration ranging from about 20 to about 900 mEq/L; a buffer; water; chloride at a concentration ranging from about 1,000 to about 7,000 mEq/L; and at least one physiologically-acceptable cation.

2. The composition of claim 1 wherein the buffer comprises a buffering anion selected from acetate and lactate.

3. The composition of claim 1 wherein the buffer comprises a buffering anion selected from acetate and lactate at a concentration ranging from about 0.01 to about 150 mEq/L.

4. A precursor composition for preparing a buffered dialysate, the precursor composition having a pH of 1–4 and comprising water; chloride at a concentration ranging from about 1,000 to about 7,000 mEq/L; citrate at a concentration ranging from about 20 to about 900 mEq/L; at least one buffering anion selected from acetate and/or lactate at a concentration ranging from about 0.01 to about 150 mEq/L; and at least one physiologically-acceptable cation.

5. The precursor composition of claim 4 comprising citrate at a concentration ranging from about 70 to about 150 mEq/L.

6. The precursor composition of claim 4 wherein the buffering anion is acetate at a concentration ranging from about 0.3 to about 125 mEq/L.

7. The precursor composition of claim 4 wherein the buffering anion is lactate at a concentration ranging from about 0.3 to about 125 mEq/L.

8. The precursor composition of claim 4 wherein the physiologically-acceptable cation is selected from a group consisting of hydrogen, sodium, potassium, calcium, magnesium, and combinations thereof.

9. The precursor composition of claim 4, further comprising a sugar selected from glucose, a poly(glucose), and fructose at a concentration of less than about 2,700 g/L.

10. The precursor composition of claim 4 wherein the citrate is in the form of at least one of citric acid and a salt thereof selected from a group consisting of sodium dihydrogen citrate, disodium hydrogen citrate, trisodium citrate, trisodium citrate dihydrate, potassium dihydrogen citrate, dipotassium hydrogen citrate, calcium citrate, and magnesium citrate; wherein the buffering anion acetate is in the form of at least one of acetic acid and a salt thereof selected from a group consisting of sodium acetate, sodium acetate trihydrate, potassium acetate, calcium acetate, calcium acetate monohydrate, magnesium acetate, and magnesium acetate tetrahydrate; and wherein the buffering anion lactate is in the form of at least one of lactic acid and a salt thereof selected from a group consisting of sodium lactate, potassium lactate, calcium lactate and magnesium lactate trihydrate.

11. The precursor composition of claim 4 wherein the water meets or exceeds the purity requirements established by the Association for the Advancement of Medical Instrumentation (AAMI) for dialysate, and all other components have at least United States Pharmacopeia (USP)-grade purity.

12. The precursor composition of claim 4 having a pH ranging from about 2 to about 4 at a temperature of about 15° C. to about 40° C.

13. The precursor composition of claim 4 comprising chloride at a concentration ranging from about 2,000 to about 5,000 mEq/L; citrate at a concentration ranging from about 70 to about 150 mEq/L; acetate at a concentration ranging from about 0.3 to about 125 mEq/L; at least one physiologically-acceptable cation selected from hydrogen, sodium at a concentration ranging from about 2,000 to about 5,000 mEq/L, potassium at a concentration of less than about 250 mEq/L, calcium at a concentration of less than about 250 mEq/L, and magnesium at a concentration of less than about 100 mEq/L; and glucose at a concentration of less than about 2,700 g/L, where the composition at least meets the AAMI standard set for dialysate.

14. A method of forming a dialysate precursor composition comprising mixing treated water, chloride, citrate, at least one buffering anion selected from acetate and/or lactate, and at least one physiologically-acceptable cation to provide a composition having chloride at a concentration ranging from about 1,000 to about 7,000 mEq/L, citrate at a concentration ranging from about 20 to about 900 mEq/L, and at least one buffering anion selected from acetate and lactate at a concentration ranging from about 0.01 to about 150 mEq/L to provide dialysate precursor composition having a pH of 1–4.

15. The method of claim 14 comprising citrate at a concentration ranging from about 70 to about 150 mEq/L.

16. The method of claim 14 wherein the buffering anion is acetate at a concentration ranging from about 0.3 to about 125 mEq/L.

17. The method of claim 14 wherein the buffering anion is lactate at a concentration ranging from about 0.3 to about 125 mEq/L.

18. The method of claim 14 wherein the physiologically-acceptable cation is selected from a group consisting of hydrogen, sodium, potassium, calcium, magnesium, and combinations thereof.

19. The method of claim 14, further comprising mixing the dialysate precursor with a sugar selected from glucose, poly(glucose) and fructose, at a concentration of less than about 2,700 g/L.

20. The method of claim 14 wherein the citrate is in the form of at least one of citric acid or a salt thereof selected from a group consisting of sodium dihydrogen citrate, disodium hydrogen citrate, trisodium citrate, trisodium citrate dihydrate, potassium dihydrogen citrate, dipotassium hydrogen citrate, calcium citrate, and magnesium citrate.

21. The method of claim 14 wherein the buffering anion acetate is in the form of at least one of acetic acid or a salt thereof selected from a group consisting of sodium acetate, sodium acetate trihydrate, potassium acetate, calcium acetate, calcium acetate monohydrate, magnesium acetate, and magnesium acetate tetrahydrate.

22. The method of claim 14 wherein the buffering anion lactate is in the form of at least one of lactic acid or a salt thereof selected from a group consisting of sodium lactate, potassium lactate, calcium lactate and magnesium lactate trihydrate.

23. The method of claim 14, further comprising mixing the dialysate precursor composition with treated water, wherein the treated water meets or exceeds the purity requirements established by AAMI for dialysate, and all other components have at least USP-grade purity.

24. The method of claim 14 comprising chloride at a concentration ranging from about 2,000 to about 5,000 mEq/L; citrate at a concentration ranging from about 70 to about 150 mEq/L; acetate at a concentration ranging from about 0.3 to about 125 mEq/L; at least one physiologically-acceptable cation selected from hydrogen, sodium at a concentration ranging from about 2,000 to about 5,000 mEq/L, potassium at a concentration of less than about 250 mEq/L, calcium at a concentration of less than about 250 mEq/L, magnesium at a concentration of less than about 100 mEq/L; and dextrose at a concentration of less than about 2,700 g/L, where the composition meets or exceeds the AAMI-quality standard set for dialysate.

25. A composition prepared according to the method of claim 14.

* * * * *

(12) EX PARTE REEXAMINATION CERTIFICATE (7097th)
United States Patent
Callan et al.

(10) Number: US 6,610,206 C1
(45) Certificate Issued: Oct. 6, 2009

(54) BUFFERED COMPOSITIONS FOR DIALYSIS

(75) Inventors: Robin Callan, Bellevue, WA (US); Walter A. van Schalkwijk, Issaquah, WA (US); James J. Cole, Arlington, WA (US)

(73) Assignee: Advanced Renal Technologies, Bellevue, WA (US)

Reexamination Request:
No. 90/009,252, Aug. 15, 2008

Reexamination Certificate for:
Patent No.: 6,610,206
Issued: Aug. 26, 2003
Appl. No.: 09/421,622
Filed: Oct. 19, 1999

Related U.S. Application Data

(60) Provisional application No. 60/105,049, filed on Oct. 20, 1998.

(51) Int. Cl.
*A61K 31/19* (2006.01)
*A61K 31/185* (2006.01)
*A61K 33/14* (2006.01)
*A61K 33/26* (2006.01)
*A61K 45/00* (2006.01)
*A61K 45/06* (2006.01)
*A61M 1/16* (2006.01)
*A61M 1/28* (2006.01)

(52) U.S. Cl. .................. 210/646; 210/647; 424/665; 514/557; 514/574

(58) Field of Classification Search .............. None
See application file for complete search history.

(56) References Cited

U.S. PATENT DOCUMENTS

| 5,032,615 | A | 7/1991 | Ward et al. | 514/574 |
| 2004/0060865 | A1 | 4/2004 | Callan et al. | 210/646 |
| 2005/0119598 | A1 | 6/2005 | Callan et al. | 604/5.01 |

FOREIGN PATENT DOCUMENTS

| DE | 41 14 908 A1 | 11/1992 |
| DE | 196 54 746 A1 | 7/1998 |
| EP | 0 022 922 A1 | 1/1981 |
| EP | 0 457 960 A2 | 11/1991 |
| EP | 0 564 672 A1 | 10/1993 |
| EP | 1 059 083 A2 | 12/2000 |
| JP | 10-87478 A | 4/1998 |
| JP | 10-87478 | 4/1998 |
| WO | WO 92/11046 A1 | 7/1992 |
| WO | WO 98/06482 A1 | 2/1998 |
| WO | WO 98/29434 A1 | 7/1998 |
| WO | WO 99/07419 A1 | 2/1999 |
| WO | WO 01/21233 A1 | 3/2001 |
| WO | WO 2005/002599 A1 | 1/2005 |

OTHER PUBLICATIONS

Ahmad et al., "Increased Dialyzer Efficiency Using a Dialysate Containing Citric Acid in Place of Acetic Acid," *J. Am. Soc. Nephrol. 10*: 188A, Abstract A0961, 1999.

Apsner et al., "A Simple Method for Citrate Anticoagulation (CA) during High Flux Dialysis: Experience with 760 Dialyses in 34 Patients," *J. Am. Soc. Nephrol. 10*: 188A, Abstract A0962, 1999.

Drukker et al., *Replacement of Renal Function By Dialysis*, Fourth Edition, Kluwer Academic Publishers, Dordrecht, The Netherlands, 1996, p. 345.

European Pharmacopoeia Commission, "Peritoneal Dialysis, Solutions For," in *European Pharmacopoeia*, $3^{rd}$ edition, Strasbourg, Germany, Council of Europe, 1997, pp. 1301–1303.

Golberg, "Pharmacology of Parenteral Iron Preparations," in Wallerstein and Mettier (eds.), *Iron in Clinical Medicine*, University of California Press, Berkeley and Los Angeles, 1958, pp. 74–92.

Jander and Blasius, *Lehrbuch der analytischen und präparativen anorganischen Chemie* (translated *Text book of analytical and preparative inorganic chemistry*), S. Hirzel Verlag Stuttgart, Germany, 1973, $10^{th}$, revised edition, Chapter 2.6.5.5.4, "Buffer Capacity," p. 66, translation.

Derwent World Patent Index, Accession No. 1996–235949.

*Primary Examiner*—Gary L Kunz

(57) ABSTRACT

Acid concentrates, and dialysate compositions prepared therefrom, contain citric acid and an effective amount of a buffering agent selected from acetate and/or lactate. The buffering agent allows a physiologically acceptable amount of citrate to maintain the desired pH of the dialysate.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 2, lines 47–54:

In one embodiment, the invention provides a dialysate precursor composition. This composition contains, at a minimum, water; chloride at a concentration ranging from about 1,000 to about 7,000 mEq/L; citrate at a concentration ranging from about 20 to about [900 ] *200* mEq/L; at least one buffering anion selected from acetate and/or lactate at a concentration ranging from about 0.01 to about 150 mEq/L; and at least one physiologically-acceptable cation.

Column 2, lines 63–Column 3, line 6:

In another embodiment, the present invention provides a method of forming a dialysate precursor composition. The method includes the step of mixing together treater water, chloride, citrate, at least one buffering anion selected from acetate and/or lactate, and at least one physiologically-acceptable cation to provide a composition having chloride at a concentration ranging from about 1,000 to about 7,000 mEq/L, citrate at a concentration ranging from about 20 to about [900] *200* mEq/L, and at least one buffering anion selected from acetate and lactate at a concentration ranging from about 0.01 to about 150 mEq/L.

Column 5, lines 27–36:

Citrate has been previously recognized to be able to function as an anti-coagulant in the bloodstream by binding calcium. Accordingly, the citrate concentration of the dialysate precursor composition should be selected in view of its anti-coagulation properties. Unless other measures are taken, the citrate concentration should not exceed about [900 mEq/L, and is preferably not more than about 200 mEq/L. When citrate concentrations of 200–900 mEq/L are employed, the magnesium and/or calcium concentration of the dialysate precursor composition must be increased] *200 mEq/L*.

Column 5, lines 37–51:

Although the citrate concentration should not be so great that is detrimentally affects the coagulation properties of blood, the concentration of citrate should be sufficiently high that it will be effective to achieve and maintain the pH of the final dialysate composition at a physiologically-acceptable pH. Typically, a citrate concentration that is one-quarter or less of the amount needed to achieve anti-coagulation can provide a dialysate composition with a physiologically-acceptable pH. Thus, the present dialysate precursor composition should have a minimum citrate concentraton of about 20 mEq/L in order to provide the desired dialysate pH. In one embodiment, the dialysate precursor composition contains citrate at a concentration ranging from about 20 to about [900] *200* mEq/L and in a preferred embodiment the composition contains citrate at a concentration ranging from about 70 to about 150 mEq/L.

Column 6, lines 36–47:

In general, the dialysate precursor composition will typically contain more equivalents of citrate than equivalents of buffering anion. The precursor composition preferably contains more equivalents of citrate than equivalents of acetate, lactate, or acetate+lactate. In one embodiment, the dialysate precursor composition contains citrate at a concentration ranging from about 20 to about [900] *200* mEq/L together with a buffering anion selected from acetate and/or lactate at a concentration ranging from about 0.01 to about 150 mEq/L. In a preferred embodiment the composition contains citrate from about 70 to about 150 mEq/L and a buffering anion selected from acetate and/or lactate at a concentration ranging from about 0.3 to about 125 mEq/L.

Column 9, lines 12–21:

In one embodiment, the invention provides a method of forming a dialysate precursor composition which includes the step of mixing water, chloride, citrate, at least one buffering anion selected from acetate and/or lactate, and at least one physiologically-acceptable cation, to provide a composition having chloride at a concentration ranging from about 1,000 to 7,000 mEq/L, citrate at a concentration ranging from about 20 to [900] *200* mEq/L, and at least one buffering anion selected from acetate and/or lactate at a total concentration ranging from about 0.01 to 150 mEq/L.

AS A RESULT OF REEXAMINATION, IT HAS BEEN DETERMINED THAT:

Claims 1–3 are cancelled.

Claims 4 and 14 are determined to be patentable as amended.

Claims 5–13 and 15–25, dependent on an amended claim, are determined to be patentable.

4. A precursor composition for preparing a buffered dialysate, the precursor composition having a pH of 1–4 and comprising water; chloride at a concentration ranging from about 1,000 to about 7,000 mEq/L; citrate at a concentration ranging from about 20 to about [900] *200* mEq/L; at least one buffering anion selected from acetate and/or lactate at a concentration ranging from about 0.01 to about 150 mEq/L; and at least one physiologically-acceptable cation.

14. A method of forming a dialysate precursor composition comprising mixing treated water, chloride, citrate, at least one buffering anion selected from acetate and/or lactate, and at least one physiologically-acceptable cation to provide a composition having chloride at a concentration ranging from about 1,000 to about 7,000 mEq/L, citrate at a concentration ranging from about 20 to about [900] *200* mEq/L, and at least one buffering anion selected from acetate and lactate at a concentration ranging from about 0.01 to about 150 mEq/L to provide dialysate precursor composition having a pH of 1–4.

* * * * *